United States Patent [19]

Piotrowski et al.

[11] Patent Number: 5,059,703

[45] Date of Patent: Oct. 22, 1991

[54] HYDROCARBON SOLUBLE COPPER ALKOXIDE COMPOSITIONS

[75] Inventors: Andrzej M. Piotrowski, Houston; Dennis B. Malpass, La Porte, both of Tex.

[73] Assignee: Texas Alkyls, Inc., Deer Park, Tex.

[21] Appl. No.: 334,637

[22] Filed: Apr. 7, 1989

Related U.S. Application Data

[63] Continuation of Ser. No. 129,796, Dec. 7, 1987, Pat. No. 4,847,239.

[51] Int. Cl.$^5$ .................................................. C07F 1/08
[52] U.S. Cl. .................................... 556/113; 502/150; 502/171
[58] Field of Search ................ 508/801, 802; 556/113; 502/150, 171

[56] References Cited

U.S. PATENT DOCUMENTS

| | | | |
|---|---|---|---|
| 3,006,941 | 10/1961 | Mudrak | 502/171 |
| 3,056,818 | 10/1962 | Werber | 502/171 |
| 3,277,002 | 10/1966 | Hurt et al. | 252/18 |
| 3,403,163 | 9/1968 | Fuchsman | 556/113 |
| 3,538,168 | 11/1970 | Mitchell | 556/113 |
| 4,698,323 | 10/1987 | Band et al. | 502/133 |
| 4,837,190 | 6/1989 | Summers, III et al. | 502/171 |

OTHER PUBLICATIONS

Horowitz et al., Sub Micrometer Superconducting $VBa_2Cu_3O_{6+x}$ Particles Made by a Low Temperature Synthetic Route; Science, vol. 243, pp. 66-69, Jan. 6, 1989.

Material and Processing Report, vol. 2, No. 10, Jan. 1988; pp. 5-7.

*Primary Examiner*—Patrick P. Garvin
*Assistant Examiner*—E. D. Irzinski
*Attorney, Agent, or Firm*—Richard P. Fennelly; Louis A. Morris

[57] ABSTRACT

Copper alkoxy alkoxides of the formula CuOR or Cu(OR)$_2$, where R is derived from an alkoxy alkanol of from 3 to 8 carbon atoms, are superconducting ceramic precursors. They can be formed by reacting an alkoxy alkanol with a copper alkoxide. Compositions containing theser alkoxides solubilized in an organic solvent, such as toluene, can be prepared by the additional use of a barium alkoxide solubilization agent.

4 Claims, No Drawings

HYDROCARBON SOLUBLE COPPER ALKOXIDE COMPOSITIONS

This is a continuation of application Ser. No. 129,796 filed Dec. 7, 1987, now U.S. Pat. No. 4,847,259.

BACKGROUND OF THE INVENTION

1. Field of the Invention

The present invention relates to soluble copper alkoxide compositions useful, for example, as a superconducting ceramic precursor.

2. Description of the Prior Art

Recent advances in superconductor metal oxide technology have identified the composition $YBa_2Cu_3O_y$, where y can range from 6.4 to 7.1, as a potential superconductor of high interest. It would be of interest to be able to provide a soluble copper alkoxide reagent which could function as a precursor for such a composition, if it were to be made by chemical means (e.g., using sol-gel technology) from such an alkoxide.

G. M. Whitesides et al., in J. Amer. Chem. Soc., 96:9 (May 1, 1974), pp. 2829–2835 mentions the synthesis of certain copper (I) alkoxides. It indicates that, with the exception of copper (I) methoxide, the copper (I) alkoxides were soluble in ether at 0° C. and that most were also soluble in hydrocarbon solvents, although copper (I) cyclohexoxide and cyclopentoxide provided notable exceptions. Whitesides et al. cited earlier work by G. Costa et al. appearing in J. Inorg. Nucl. Chem., 1965, Vol. 27, pp. 281–285 relating to the insolubility of copper (I) methoxide. T. Tsuda et al., in J. Amer. Chem. Soc. 94:2, January 26, 1972, pp. 658–659 identify cuprous tert-butoxide as being soluble in organic solvents and being a new and useful metalation reagent.

U.S. Pat. No. 3,277,002 mentions certain alcohol soluble metal alkoxides, including those of copper, which are formed by a double decomposition reaction using sodium methoxide and a metal salt. This reaction produces the corresponding sodium salt as a by-product. The alcohols which can be used to form the sodium alkoxide starting reagent include alkoxy alkanols (see Col. 6, lines 10–22).

Related Application

Pending European Patent Application No. 87200842.0, filed May 8, 1987 and published under Publication No. 244,917 on November 11, 1987, describes certain organic solvent soluble, alkoxy alkoxides of Mg, Ca, Sr, Ba, Sc, y and La where the ligand connected to the metal atom through the oxygen atom is derived from an alkoxy alkanol.

SUMMARY OF THE PRESENT INVENTION

It has been found that copper alkoxy alkoxides, which are sparingly soluble in organic solvents, can be made highly soluble by the addition of a barium alkoxide solubilizing agent.

DETAILED DESCRIPTION OF THE INVENTION

The copper alkoxy alkoxides contemplated for use by the current invention encompass compounds of the formulae $Cu(OR)_2$ and $CuOR$, where R is derived from an alkoxy alkanol such as 3-methoxybutanol or 2-methoxypropanol. Generally, the total carbon content of R can range from about 3 to about 8. The alkoxy moiety on this ligand is advantageously methoxy. These copper (I) and (II) alkoxy alkoxides can be formed by a novel exchange reaction using a copper alkoxide (e.g., copper methoxide) and an appropriate alkoxy alkanol (e.g., an alkoxy propanol or butanol) in a suitable organic solvent, such as toluene. Such a procedure avoids generation of the type of sodium salt by-product shown in U.S. Pat. No. 3,277,002. This can be important if the materials are intended, for example, for superconductor applications where either sodium or its related anion cannot be tolerated as impurities.

As indicated before, these copper alkoxy alkoxides in most cases have only slight solubility in hydrocarbon organic solvents, such as toluene. However, in order to increase their degree of solubility, and, hence, their degree of potential utility, the present invention also contemplates the additional presence, in the solvent/copper alkoxy alkoxide composition, of an effective amount of a barium alkoxide solubilizing agent. These agents have the formula $Ba(OR^1)_2$, where R is an alkyl group of from about 3 to about 8 carbon atoms. Representative branched chain R groups which have been found to be useful in accordance with the present invention are 2-ethylhexyl and 3-methoxy-butyl.

The maximum copper concentration in the final product is about 8% by weight (12.7% is the copper content in pure mixed alkoxide without any solvent) and the mole ratio of copper alkoxide to barium alkoxide can range from about 3:1 to about 1:1.

The present invention is directed to the preparation of compositions comprising either copper (I) or copper (II) species. The copper (I) species are easily formed from the copper (II) species by appropriate heating.

The present invention is further understood by reference to the Examples which follow.

EXAMPLE 1

Preparation of mixed copper (II)-barium alkoxides.

Copper methoxide (4.16 grams) was suspended in 50 milliliters of toluene and 2 molar equivalents of 3-methoxybutanol were added. The reaction mixture was refluxed briefly and some solvent was evaporated to remove methanol formed in the process of ligand exchange. Copper (II) 3-methoxybutoxide is only slightly soluble in toluene. After the addition of 2/3 molar equivalent of barium 2-ethylhexoxide in toluene, almost all solids went into solution. A dark blue solution of mixed copper-barium alkoxide was filtered (only a small amount of gray solid was left on the filter) and toluene was removed under vacuum. The resulting dark blue semisolid was dissolved in cyclohexane. The resultant solution was analyzed for barium and copper and showed 3.42% Ba and 2.55% Cu.

EXAMPLE 2

Preparation of mixed copper (II)-barium alkoxides.

Copper methoxide (0.80 grams) was suspended in 5 milliliters of toluene and a solution of barium 2-ethylhexoxide was added (copper to barium ratio =3/2). Part of the copper methoxide dissolved upon warming, but the majority of the copper methoxide remained insoluble. Two molar equivalents of 2-methoxypropanol were added. A homogeneous solution was formed after brief warming to reflux.

EXAMPLE 3

Preparation of barium bis(3-methoxy-1-butoxide).

Barium metal (14.0 grams chopped foil) was placed in a 500-milliliter flask equipped with reflux condenser and nitrogen inlet. Three milliliters of barium bis(2-ethyl-1-hexoxide) solution in toluene were added as an activator followed by 100 milliliters of dry toluene. Barium was suspended in toluene using magnetic stirring, and 22.0 milliliters of 3-methoxy-1-butanol were added over a period of ½ hour. An exothermic reaction started almost immediately. After the exotherm subsided, the contents of the flask were stirred at room temperature overnight. All metal dissolved and a grayish pink solid was formed. The solid product was separated by filtration through a glass frit coated with 5.0 grams of celite. Solids containing product and celite were then washed with toluene followed by pentane and were dried under vacuum. A total of 38.0 grams of white solid containing 34.6 weight percent barium was isolated, which is equivalent to 93% of the initial barium charged.

EXAMPLE 4

Preparation of copper (II) bis(3-methoxy-1-butoxide).

Copper chloride (63.0 grams) was dissolved in 200 milliliters of methanol and this solution was slowly added to a well-stirred solution of sodium methoxide in methanol (177 grams of 25 weight percent solution diluted with 200 milliliters of methanol). After the addition was completed, the reaction mixture was diluted with methanol to form 900 milliliters of suspension. Copper methoxide coprecipitated with sodium chloride was separated by filtration. The solid was then washed with methanol, toluene, pentane and dried in a stream of nitrogen. Such prepared copper methoxide-sodium chloride mixture was transferred into a 2-liter flask and was suspended with 1 liter of toluene. At this point, 110 milliliters of 3-methoxy-1-butanol were slowly added. The reaction mixture was then warmed to reflux by external heating and 500 milliliters of toluene/methanol were evaporated in a stream of nitrogen. Since a highly viscous suspension was formed, 200 milliliters of toluene were added. This suspension of copper bis(3-methoxy-1-butoxide) and sodium chloride was then used to prepare mixed copper (I)-barium alkoxide as described in Example 6.

EXAMPLE 5

Preparation of mixed copper (II)-barium alkoxides.

Copper (II) methoxide (1.25 grams) was suspended in 80 milliliters of toluene and two molar equivalents of 3-methoxy-1-butanol were added. The reaction mixture was refluxed for six minutes, and about 30 milliliters of toluene/methanol were allowed to evaporate in a stream of nitrogen. Barium bis(3-methoxy-1-butoxide) (2.65 grams) was added at this point and the reaction mixture was refluxed briefly under a nitrogen purge (prolonged heating leads to formation of copper (I) alkoxide). A dark blue solution containing 2.40 weight percent copper and 3.57 weight percent barium was formed.

EXAMPLE 6

Preparation of mixed copper (I)-barium alkoxides.

Barium metal (43.0 grams) in the form of chopped foil was placed in a 1-liter flask equipped with reflux condenser and nitrogen inlet. Toluene (400 milliliters) was added followed by 80 milliliters of 3-methoxy-1-butanol added in eight portions over a period of five hours. After the addition of alcohol was completed, the reaction mixture was refluxed for 1.5 hours. Such prepared suspension of barium alkoxide was combined with copper (II) 3-methoxy-1-butoxide from Example 4. After 10 minutes of stirring, a viscous, dark blue solution was formed. The reaction mixture was then refluxed for 1.5 hours, and 500 milliliters of toluene/methanol were allowed to evaporate. The resulting dark reddish brown, highly air-sensitive solution containing suspensed sodium chloride was allowed to settle overnight. A total of 600 grams of the dark blue supernatant free of solids was isolated. The solution contained 3.25 weight percent copper and 4.68 weight percent barium. This corresponds to 65% yield based on copper and same for barium.

The foregoing Examples should not be construed in a limiting sense since they are merely for illustrative purposes. The scope of protection sought is set forth in the claims which follow.

We claim:

1. A process for forming copper alkoxy alkoxides of the formula CuOR or Cu(OR)$_2$, where R is alkoxy alkyl having a total carbon content of from about 3 to about 8, by an exchange reaction which comprises reacting a copper alkoxide with an alkoxy alcohol of the formula ROH, where R is as defined above.

2. A process as claimed in claim 2 wherein R is 3-methoxybutanol.

3. A process as claimed in claim wherein R is 2-methoxypropanol.

4. A process as claimed in claim 2 wherein the copper alkoxide is copper methoxide.

* * * * *